United States Patent [19]

Lopez

[11] Patent Number: 4,931,048
[45] Date of Patent: Jun. 5, 1990

[54] MEDICAL DEVICE

[75] Inventor: George A. Lopez, Orange County, Calif.

[73] Assignee: ICU Medical, Inc., Irvine, Calif.

[21] Appl. No.: 258,846

[22] Filed: Oct. 17, 1988

Related U.S. Application Data

[63] Continuation of Ser. No. 849,148, Apr. 7, 1986, Pat. No. 4,778,453.

[51] Int. Cl.⁵ ............................................... A61M 5/00
[52] U.S. Cl. .................... 604/110; 604/198; 604/263
[58] Field of Search ............... 604/110, 187, 192, 198, 604/197, 263, 164, 171, 168

[56] References Cited

U.S. PATENT DOCUMENTS

| 3,380,448 | 4/1968 | Sadove et al. ............... 604/263 X |
| 3,658,061 | 4/1972 | Hall . |
| 3,890,971 | 6/1975 | Lesson et al. . |
| 3,943,927 | 3/1976 | Norgren . |
| 4,026,287 | 5/1977 | Haller . |
| 4,170,993 | 10/1979 | Alvarez . |
| 4,329,989 | 5/1982 | Dallons et al. . |
| 4,373,526 | 2/1983 | Kling . |
| 4,394,863 | 7/1983 | Bartner . |
| 4,553,962 | 11/1985 | Brunet . |
| 4,592,744 | 6/1986 | Jagger et al. . |
| 4,610,667 | 9/1986 | Pedicano et al. . |
| 4,631,057 | 12/1986 | Mitchell . |
| 4,654,034 | 3/1987 | Masters et al. . |
| 4,664,653 | 5/1987 | Sagstetter et al. . |
| 4,676,783 | 6/1987 | Jagger et al. ........................ 604/171 |
| 4,737,150 | 4/1988 | Baeumle et al. ................... 604/198 |

FOREIGN PATENT DOCUMENTS

| 689751 | 6/1964 | Canada . |
| 1541417 | 10/1968 | France . |
| 2134516 | 8/1972 | France . |
| 2262534 | 9/1974 | France . |
| 2178322 | 2/1987 | United Kingdom . |

Primary Examiner—John D. Yasko
Attorney, Agent, or Firm—Knobbe, Martens, Olson & Bear

[57] ABSTRACT

Disclosed is a medical device used with a syringe or the like that includes a needle protected by a guard. The needle has a connector at one end opposite its tip which enables it to be connected to the syringe. The guard is mounted on the needle and is movable axially along the shaft of the needle between a retracted position enabling the needle to be inserted into a patient and a forward position covering the tip of the needle. The guard is moved forward manually from the retracted to the forward position by the nurse after using the needle to protect the nurse against accidental needle sticks. The forward manner in which the guard is moved by the nurse eliminates the possibility of the nurse being accidentally stuck by the needle when covering the tip with the guard, because the forward movement is along the needle shaft and not inwardly toward the needle tip as with conventional practice.

19 Claims, 5 Drawing Sheets

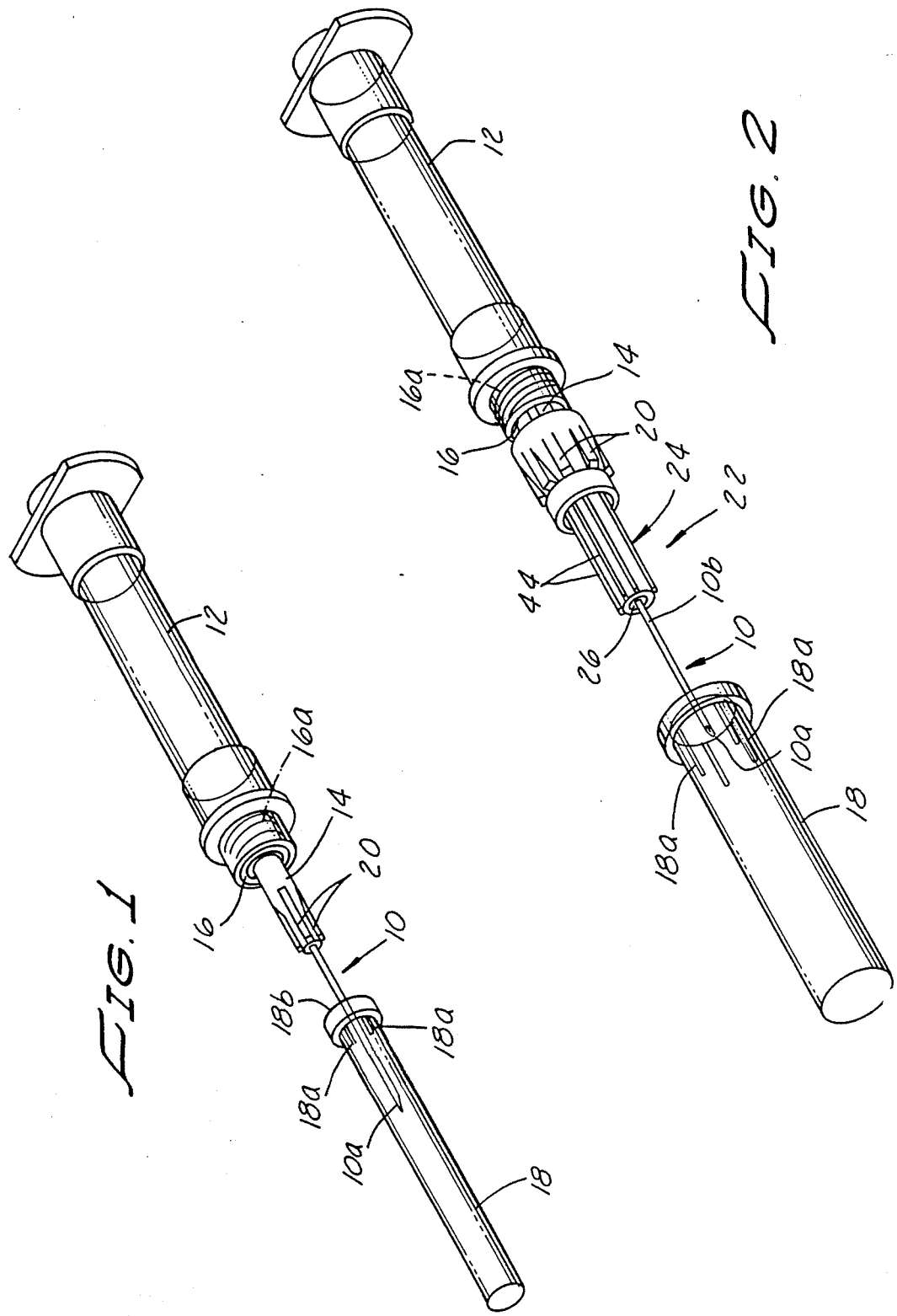

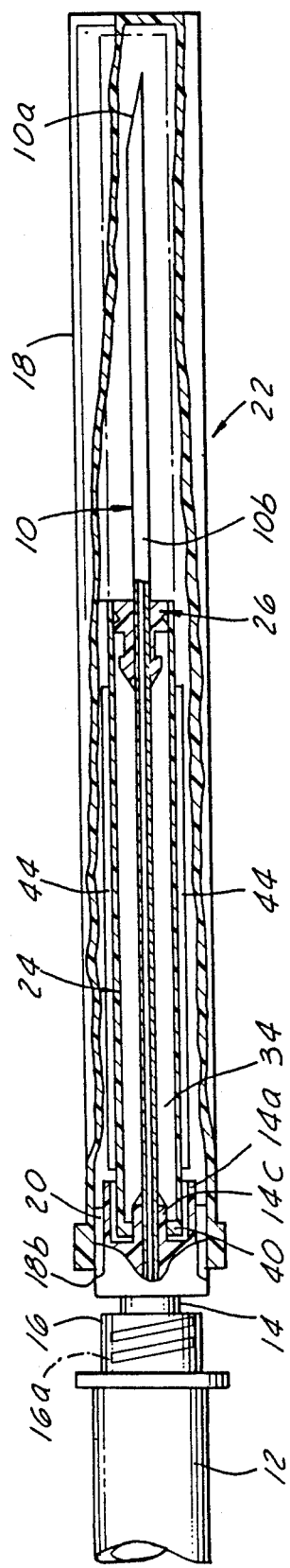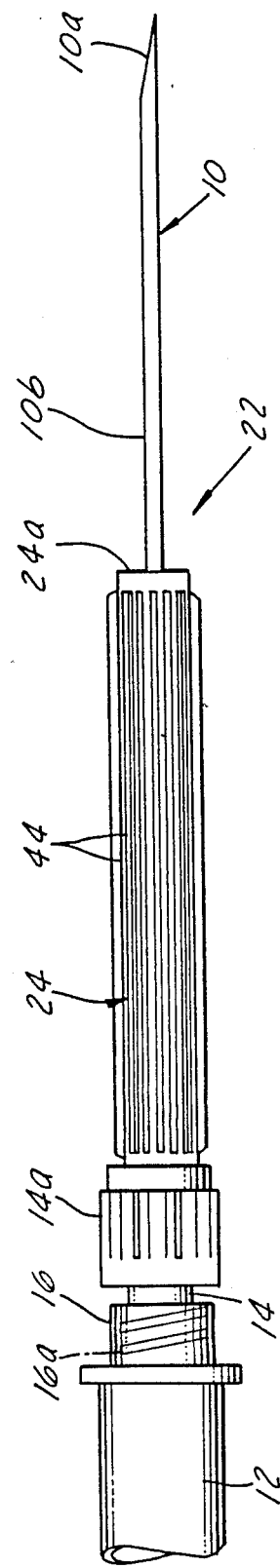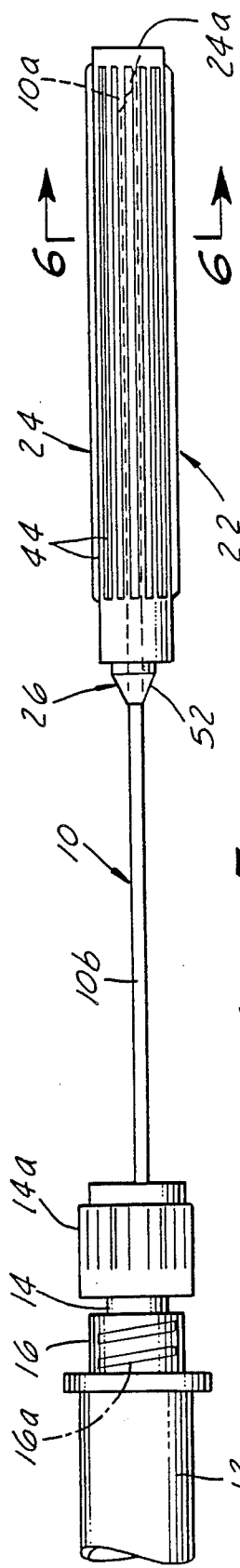

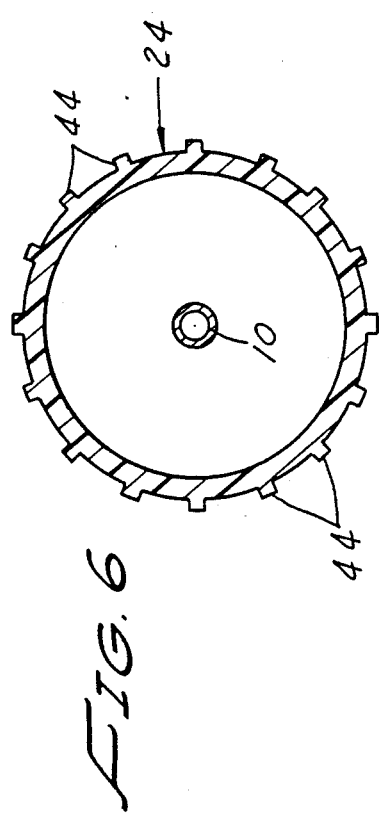
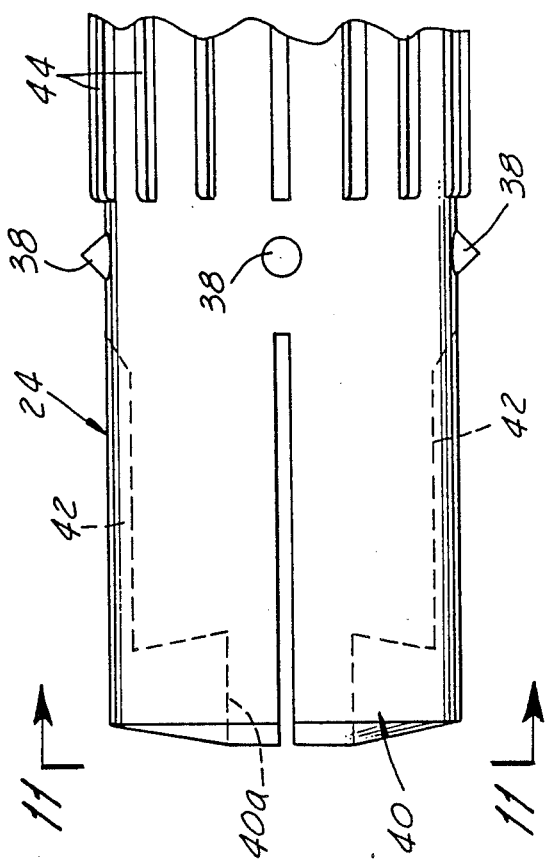
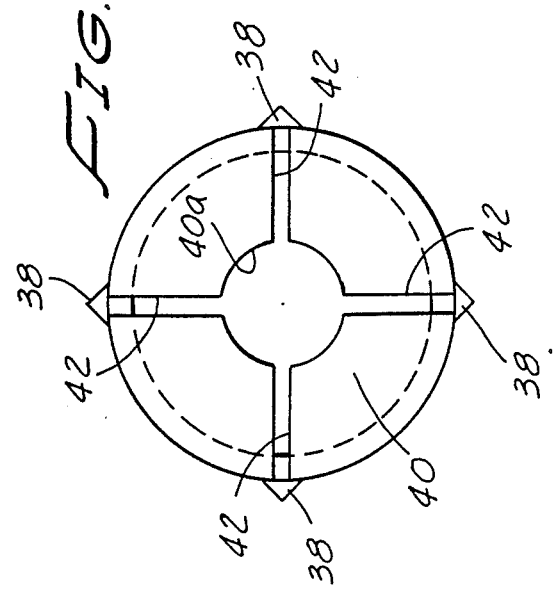

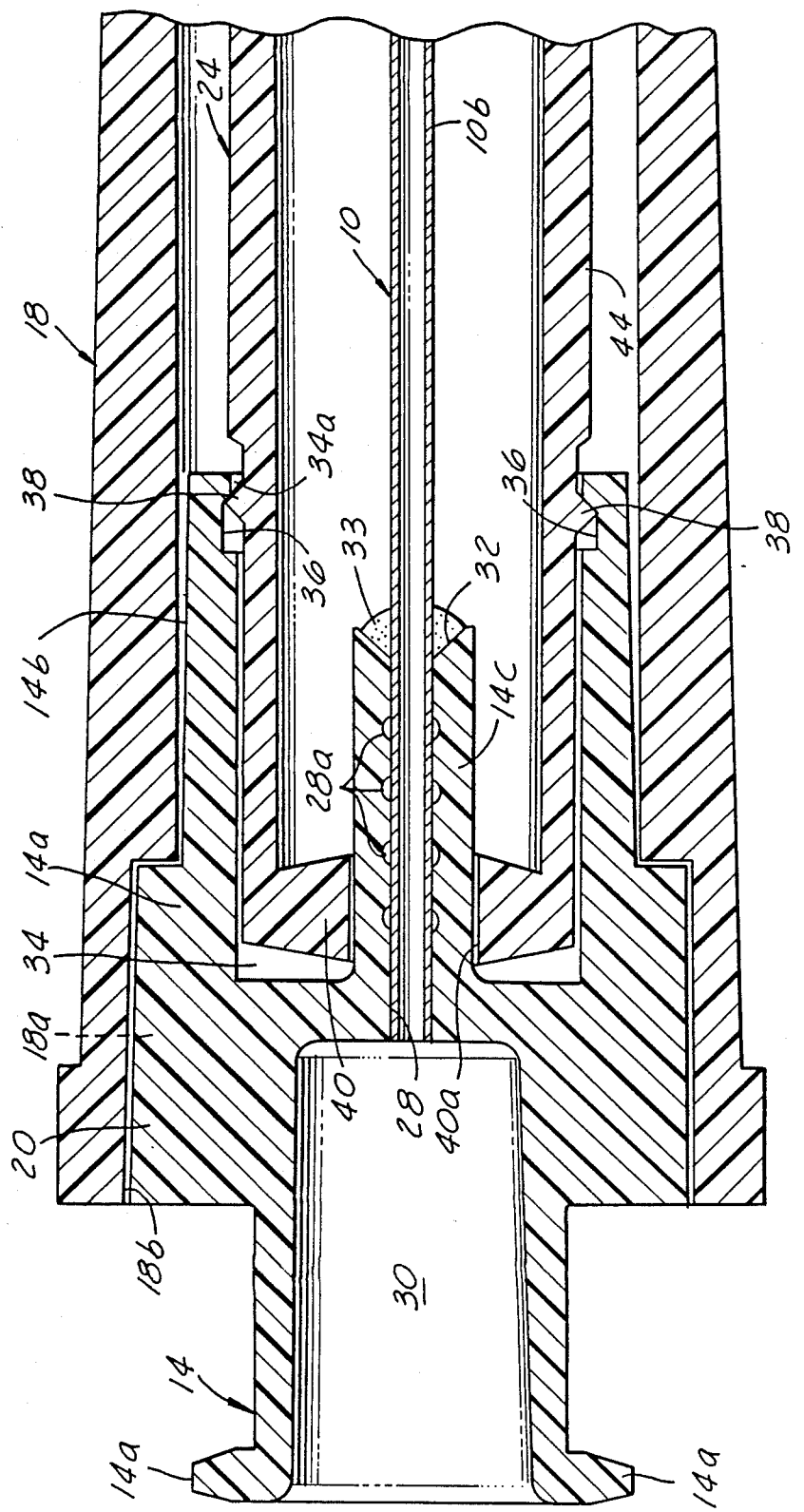

MEDICAL DEVICE

BACKGROUND OF THE INVENTION

1. Field of the Invention

This invention relates to medical devices used with, for example, syringes and intravenous (IV) medication dispenser sets and, in particular, relates to a device for enclosing a needle after it has been used so that the needle will not accidentally stick the user.

2. Background Discussion

Many medications are administered by injecting the medication through a needle that has penetrated the body of the patient. The needle is usually removeably attached to a medication dispenser such as an IV set or syringe. When the needle is attached to a syringe, the nurse manually activates a plunger which forces the medication from the syringe through the needle, out the tip of the needle, into the body of the patient. It is common practice to use disposable needles. After the needle has been used, the nurse detaches the needle from the syringe and disgards it. In many instances the nurse will clip the needle, rendering it unsuitable for subsequent use.

The needles commonly employed are contained within a sheath made, for example, of plastic. This sheath grips the needle in a fashion that allows the nurse, while holding the sheath, to attach the needle to the delivery end of the syringe. Ordinarily a Luer lock, or other type of conventional threaded device, is employed which allows the nurse to simply screw the needle onto the delivery end of the syringe. With the needle attached to the syringe, the nurse removes the sheath, exposing the needle. After the needle has been used to inject medication into the patient, the nurse frequently will replace the sheath covering the needle. Ribs on the inside of the sheath engages splines on the barrel hub of the needle upon rotation. The nurse then rotates the sheath and to detach the needle from the syringe. All too frequently in the act of resheathing the needle, the nurse accidentally sticks herself. If the patient is carrying a highly infectious disease, the nurse could be infected. Consequently, a blood test must be conducted on the nurse to see if she is already carrying the disease. This is necessary because if she is not infected at the time of the stick, her employer, the hospital, will be liable.

Accidental needle sticks have been recognized as a serious health hazard and are discussed in U. S. patent application Serial No. 06/606,679, filed May 3, 1984, entitled Medical Connector, assigned to the same assignee as this patent application. This medical connector employs a needle housed within a cap member so that the nurse is protected against accidental needle sticks. This connector, however, is not suitable for directly administering medication to the patient through a needle which is inserted into the body of the patient. Others have suggested that a protective sheath for the needle be attached to the syringe and movable to cover the needle when the needle is not in use and then retracted to expose the needle. Such devices are illustrated in U.S. Pat. Nos. 4,425,120 and 2,571,653, and 3,134,380, and 2,925,083. These devices, however, all contemplate repeated use of the needle. This would require resterilization after each use and is not consistent with current medical practices which employ disposable needles.

MAJOR FEATURES OF THE INVENTION

The problems discussed above have been obviated by the present invention which provides a simple, safe, and convenient way to protect the user against needle sticks after the needle has been used to inject medication into a patient. There are several features of this invention, no single one of which is solely responsible for its desirable attributes. Without limiting the scope of this invention, as expressed by the claims, its more prominent features will now be discussed briefly. After considering this discussion, and particularly after reading the section of this application entitled "Detailed Description of the Preferred Embodiment," one will understand how the features of this invention provide the advantages of simplicity, convenience, and safety.

One feature of the present invention is that the needle is covered with a guard after being used. The needle is secured to a connector which is adapted to be removably attached to the medication dispenser. This allows the needle to be detached and disposed after it is used. The guard is manually movable and mounted along the needle. It moves axially between a first position where the tip of the needle is exposed to a second position where the guard covers the tip of the needle and prevents needle sticks.

In accordance with another feature of this invention, locking means are mounted along the needle which permanently locks the guard in the second position upon movement of the guard from the first position to the second position. Because the guard is locked in position, there is no chance that the nurse can be stuck with the needle after she uses it. The guard is a tubular element and it has a collar at its rearward end. Associated with the guard are means which releasably hold the guard in the first position so that the nurse may apply a minimum force to overcome the grip of the holding means. After using the needle, the nurse pushes the guard towards the tip of the needle to move it to the second position. The locking means includes a receptacle for the collar and a stop which limits the forward movement of the guard. When the guard has been moved forward, the collar engages the stop and snaps into locking position in the receptacle. In this position the tip of the needle is covered by the guard. The guard has an opening in its forward and rear end which allows the guard to move axially along the needle shaft. Thus the needle tip is exposed when the guard is in the first position, but permits the guard to be pulled over the tip upon forward movement of the guard. The opening at the forward end of the guard is restricted so that a nurse will not be able to stick his or her little finger through the opening and be pricked by the tip of the needle when the guard is in the second position.

The medical device of this invention is made out of conventional plastic materials which are molded into the desired shapes, with the needle being conventional, made of a metal such as stainless steel. The device is easy to manufacture, is inexpensive, and most importantly, provides a safe way of protecting nurses against sticks from needles which have been used in administering medication to patients carrying highly infectious diseases. Once the needle has been used, the nurse simply moves the protective guard into position covering the needle, detaches the needle from the medication dispenser, and disposes of it by placing it in a suitable waste container. She does not need to clip the needle, because the guard is now permanently locked into position and one could only remove the guard by destroying the structure of the device.

The preferred embodiment of this invention illustrating all its features will now be discussed in detail. This embodiment shows the device of this invention being used with a conventional syringe. It could be used in any application where it is desired to protect a needle after it has been inserted into a patient and it is no longer desired to reuse such needle.

BRIEF DESCRIPTION OF THE DRAWING

The medical device of this invention is illustrated in the drawing, with like numerals indicating like parts, and in which:

FIG. 1 is an exploded perspective view of the conventional way of covering the disposable needle used with a syringe.

FIG. 2 is an exploded perspective view of the medical device of this invention.

FIG. 3 is a side elevational view, with sections broken away, of the medical device of this invention, with the sheath for the device in position and the guard for the needle in a retracted position.

FIG. 4 is a side elevational view of the device shown in FIG. 3, with the sheath removed.

FIG. 5 is a side-elevational view of the device shown in FIG. 4, with the guard moved to a forward position to cover the tip of the needle.

FIG. 6 is a cross-sectional view taken along line 6—6 of FIG. 5.

FIG. 7 is an enlarged fragmentary view, in cross-section, of the rear end of the device of this invention, with the guard in the retracted position.

FIG. 10 is an enlarged fragmentary view of the rear end of the guard.

FIG. 11 is a cross-sectional view taken along line 11—11 of FIG. 10.

DESCRIPTION OF THE PREFERRED EMBODIMENT

Figure 8:
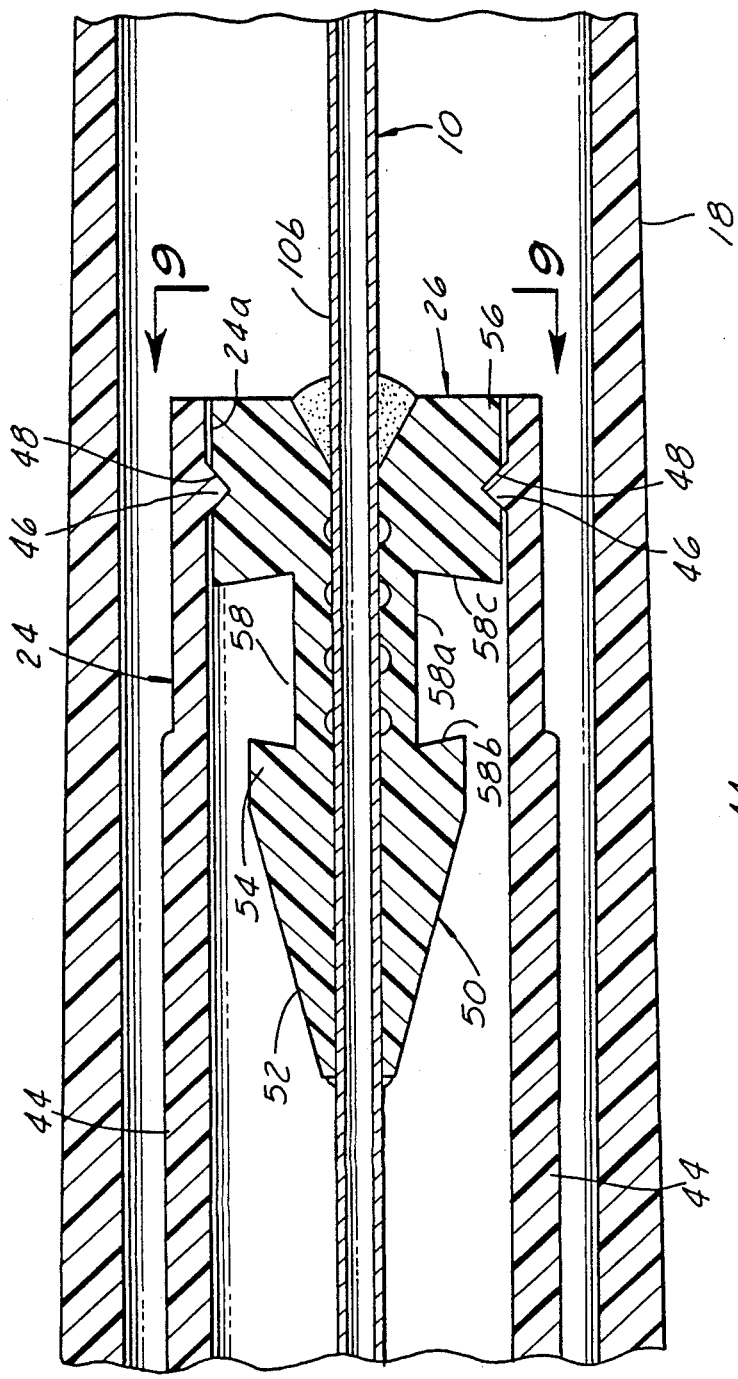
FIG. 8 is an enlarged fragmentary view in cross-section of an intermittant portion of the device, with the guard in the retracted position.

As illustrated in FIG. 1, the conventional practice for injecting medication into the body of the patient calls for a metal needle 10 to be removably attached to a syringe 12. This needle 10 has a plastic hub 14 with dog ears (not shown) that are threaded into a threaded delivery end 16 of the syringe. The needle 10 is ordinarily initially enclosed in a plastic sheath 18 which fits snugly about the hub 14. Needles 10 come in many different sizes, both in diameter and length, and they are enclosed individually within sheaths. The nurse selects which size needle to use in administering the medication and grasps the sheath 18 with one hand and then simply screws the needle 10 into position by inserting the hub 14 into the delivery end 16 of the syringe 12 and turning the sheath. The sheath 18 carries on its internal wall splines 18a which engage ribs 20 on the hub 14, enabling the sheath and needle to be rotated as a unit. With rotation, the dog ears slide into threads 16a in end 16 to lock the needle 10 on to the syringe 12. The nurse then pulls the sheath 18 off the hub 14, exposing the needle. She then inserts the needle 10 into the body of the patient, depresses a plunger (not shown) of the syringe 12 to force liquid medication through the needle, out the needle tip 10a and into the patient and then pulls the needle from the patient. Normally the nurse will replace the sheath 18, inserting the needle 10 into the open mouth 18b of the sheath. It is at this point that accidents commonly occur. If the nurse is distracted, has poor eyesight, or is simply inattentive, she may stick herself with the needle 10. If the needle 10 has just been used to inject medication into a patient infected with a highly contagious disease, it is likely that the nurse will contract this disease if she accidentally sticks herself with the needle. If she does manage to replace the sheath 18 on the needle 10 without sticking herself, she then detaches the needle 10 by turning the sheath with the hub 14 of the needle inserted snugly into open mouth 18b of the sheath 18. Rotation then occurs between the needle hub 14 and the delivery end 16 of the syringe 18 to detach the needle 10 from the syringe. In many instances, the nurse is required by hospital protocols to clip the needle before she disposes of it. This is to prevent reuse of the needle 10. Such clipping of the needle 10 creates an aerosol which may contain infectious microbes that could be enhaled by the nurse or others in the vicinity. This unsafe practice of clipping the needle and recovering it is now eliminated by the present invention.

As illustrated in FIG. 2, the medical device 22 of this invention includes a hub 14 having dog ears 14a (FIG. 7) at one end which allow the device 22 to be removably attached to the end of the syringe 12. Extending from this hub 14 is the elongated metal needle 10 of any desired length and thickness. Attached to the shaft 10a of the needle 10 is a movable guard 24 which moves axially along the shaft of the needle from a rearward position, as illustrated in FIG. 4, to a forward position, as illustrated in FIG. 5. In the forward position, the guard 24 is locked in place by means of a locking element 26 mounted to the shaft 10a of the needle 10. As best illustrated in FIG. 3, prior to use, the guard 24 is in the retracted position and the sheath 18 encases both the needle 10 and the guard.

As best shown in FIG. 7, the barrel hub 14 is molded from any suitable plastic and it has a sheath carrier forward section 14a. This section 14a preferably has a tapered side wall 14b which allows the barrel hub 14 to be inserted into the open mouth 18b of the sheath 18, with the inside wall of the sheath sitting snug against the side wall of section 14a to hold the cover in position. The barrel hub 14 has a generally cylindrical configuration and has a passageway 28 extending from the end of the hub connected to the syringe 12 to the end of the hub carrying the needle. This passageway 28 is centrally located along the longitudinal axis of the hub 14 and provides a conduit for the medication to flow from the syringe 12 into the needle 10.

The hub 14 includes a fluid reservoir 30, with the passageway 28 having a series of parallel, bores 28a running about the passageway. The passageway 28 ends in a funnel-like open section 32. One end of the needle 10 is inserted into the passageway 28 and stops at the base of the reservoir 30. An adhesive 33 is inserted through the open section 32 and flows around the outside wall of the needle shaft 10a and into the bores 28a filling them. On curing, the adhesive 33 bonds the needle 10 into position securely.

The end of the barrel hub 14 opposite the reservoir 30 includes a cavity 34 with an open mouth 34a into which the rear of the guard 24 will pass. The cavity 34 is formed by an annular recess within the hub section 14a.

There is a circumferential groove 36 adjacent the mouth 34 which engages a row of spaced nipples 38 (FIG. 10) carried on the exterior of the rear end of the guard 24. Centrally located, and integral with the hub section 14a, is a neck portion 14c through which the passageway 28 extends. This neck portion 14c is of a generally cylindrical configuration.

The guard 24 is a generally hollow cylindrical member made of plastic having at its rear end a collar member 40 in the form of a annular wall which is received within the cavity 34 when the guard is in the retracted position. The neck member 14c extends through an opening 40a in the collar 40, with the internal annular surface of the collar abutting the external surface of the neck 14c. The guard 24 has an open end 24a (FIG. 8) which is sufficiently restricted so that a typical adult user cannot insert his or her finger through this opening and contact the tip 10a of the needle 10. Typically the diameter of this opening is less than one centimeter and the tip 10a of the needle is displaced inwardly from this opening a minimal distance of one-half centimeter.

As best illustrated in FIGS. 10 and 11, the rear end of the guard 24 has four equally spaced slits 42 extending lengthwise from the rear end to about the nipples 38. Each slit 42 terminates in a beveled end. These slits divide the collar 40 into four equal segments, which will flex outwardly, enlarging the opening 40a as the guard 24 engages the locking element 26. This feature will be explained in greater detail subsequently. A series of parallel ribs 44 molded in the exterior surface of the guard 24 to provide means for facilitating grasping and holding the guard. At the open end 24a of the guard 24 is an annular ridge 46 carried on the inside wall of the guard. This ridge has tapered side walls which are received in a corresponding tapered groove 48 in the locking element 26. The nipples 38 and ridge 46 hold the guard 24 in the rearward position until the nurse manually moves the guard forward to the position shown in FIG. 5. Thus there is enough play to allow the guard to be moved forward manually, but sufficient tightness so that the guard will not accidentally jar loose, for example, during shipment.

Figure 9:
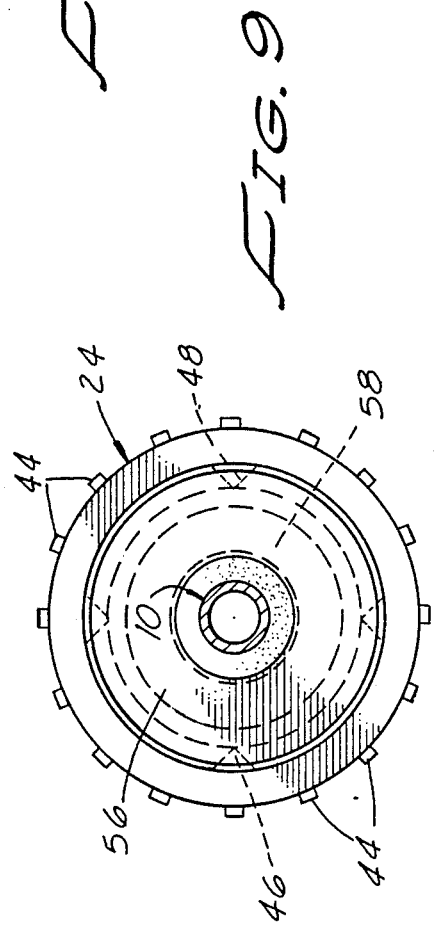
FIG. 9 is a cross-sectional view taken along line 9—9 of FIG. 8.

The locking for the guard 24 is best illustrated by FIGS. 8 through 11. The locking element as shown in FIGS. 8 and 9 includes a body member 50 having a conical-like end portion 52 which provides a ramp over which the collar 40 rides as the guard is moved to the fully extended forward position. This ramp terminates in an annular rear shoulder 54. At the other end of the body member 50 is an annular front shoulder 56. The front shoulder 56 is higher than the rear shoulder 54 and its diameter is just slightly less than the diameter of the open mouth 24a of the guard. Between the shoulders 54 and 56 is a receptacle portion 58 which consists of an annular recess running about the central portion of the body member 50 having a base 58a and opposed inwardly tapered rear and front walls 58b and 58c. The collar 40 drops into this receptacle portion 58 when the guard 24 is moved to the fully extended forward position shown in FIG. 5. The collar segments spread apart slightly as the guard 24 moves up the ramp end 52. Thus, the opening 40a in the collar 40 expands slightly to allow this end 52 to pass through this opening with the collar riding up and over the shoulder 54. When the collar 40 is opposite the receptacle portion 58, the opening 40a will resume its ordinary diameter and the collar 40 drops into the receptacle portion, with the front tapered wall 58c acting as a stop which abuts the collar.

Once the collar 40 is in the receptacle portion 58, the guard is permanently locked into position so that it cannot move rearwardly to return to the position shown in FIG. 4.

OPERATION

To use of the medical device of this invention, one would first attach it to the delivery end 16 of the syringe 12, as shown in FIG. 3, inserting the dog ears 14a into the threads 16a in delivery end of the syringe and turning the device 22 to screw it in position. The nurse would then remove sheath 18 by simply pulling it off the barrel hub 14.

The tip 10a of the needle 10 is now exposed, as shown in FIG. 4. The nurse then penetrates the body of the patient, depresses the plunger of the syringe 18 to force medication through the passageway 28 and out the tip 10a of the needle into the body of the patient. After the medication has been administered to the patient, the nurse pulls the needle from the patient. Instead of placing the sheath back on the device 22, the nurse simply grasps an intermediate portion of the guard 24, which is in the position illustrated in FIG. 4, and pushes it forward in a smooth, one stroke motion. Even if the nurse's hand slipped from the guard 24, her fingers would simply ride down the shaft 10b of the needle 10 and over the tip 10a of the needle, without sticking herself. This is contrary to the conventional practice where the nurse's hand moves in a direction towards the tip 10a of the needle 10.

As the nurse pushes on the guard, it will move to the right, as shown in FIG. 4, moving from the retracted position, as shown in FIG. 6, to the forward position, as shown in FIG. 5. When the nurse initiates this movement of the guard 24, the nipples 38 slips from the groove 36 and the ridge 46 slips from the groove 48. The shoulder 56 of the locking member provides stability and guidance for the guard 24 as it moves along the shaft 10b of the needle 10. When the collar engages the ramp end 52, the tip of the ramp end is inserted into the opening 40a, spreading the collar apart, slightly enlarging this opening 40a as the collar rides up the ramp and over the rear shoulder 54. When the collar 40 is opposite the receptacle portion 58, the opening will once again close and the collar 40 will snap into the receptacle portion. Because of the tapered sidewalls of the walls of the receptacle portion and corresponding tappered walls of the collar the guard is locked into position. Thus, even if the nurse attempted to retract the guard by moving it to the position shown in FIG. 4, the collar 40, locked into position in the receptacle portion 58, will prevent the guard 24 from being returned to the retracted position. Thus, the guard 24 is permanently locked into position, protecting the nurse against accidental needle sticks. Because the guard 24 cannot be moved without destroying the entire structure of the device 22, and destroying the needle, it is not necessary to clip the needle. Thus, a dangerous germ containing aerosol is not sprayed into the atmosphere.

SCOPE OF THE INVENTION

The above description presents the best mode contemplated upon carrying out the present invention. This invention is, however, susceptable to modifications and alternate constructions from the embodiments shown in the drawing and described above. Consequently, it is not the intention to limit this invention to the particular embodiments disclosed. On the contrary, the intention is to cover all modifications and alternate constructions coming within the spirit and scope of the invention as expressed by the claims.

What is claimed:

1. A medical device, comprising:
   a needle having first and second ends and a hollow shaft therebetween;
   a guard member movable axially along said needle from a first position in which the second end of said needle is exposed, to a second position in which said guard member shields said second end of said needle to prevent needle sticks; and
   locking means disposed between said first and second ends of said needle for interacting with said guard to permanently lock said guard in said second position upon movement of said guard from said first position.

2. A medical device as in claim 1, wherein said locking means is secured to said needle.

3. A medical device as in claim 2, wherein said locking means comprises a ramp which extends radially outwardly in the distal direction.

4. A medical device as in claim 2, wherein said locking means comprises an annular conical portion, extending radially outwardly in a distal direction, and terminating in a rear shoulder defining the proximal boundary of an annular groove.

5. A medical device as in claim 1, further comprising a connector secured to the first end of said needle for releasably securing said needle in fluid communication with the delivery end of a syringe.

6. A medical device as in claim 5, wherein both of said first and second positions of said guard member are beyond the delivery end of said syringe.

7. A medical device in claim 1, further comprising means for releasably retaining said guard in said first position.

8. A safety device for delivering a medication, comprising:
   a tubular hub adapted to be removably secured to the delivery end of a syringe and having a central passageway therethrough;
   an elongate needle extending from said hub and in fluid communication with said syringe;
   a tubular guard member disposed about said needle and axially movable from a first position in which the delivery end of said needle is exposed and a second position in which the delivery end of said needle is shielded against needle sticks, said guard member comprising a radially inwardly extending projection; and
   a locking element secured to said needle distally of the delivery end of said syringe, said locking element comprising a recess adapted to receive said projection when the guard member is in the second position.

9. A safety device as in claim 8, wherein both of said first and second positions of said guard member are beyond the delivery end of said syringe.

10. A medical device, comprising;
    a needle having a first and second end and a hollow shaft therebetween;
    a guard member movable axially along said needle from a first position in which the second end of said needle is exposed, to a second position in which said guard member shields said second end of said needle to prevent needle sticks; and
    a locking element disposed between said first and said second ends of said needle;
    wherein said locking element comprises a tapered portion which increases in cross-sectional area in the distal direction, terminating in a first shoulder defining the proximal boundary of an annular recess therein.

11. A medical device as in claim 10, wherein said locking element further comprises a second annular shoulder defining the distal boundary of said annular recess.

12. A medical device as in claim 10, wherein said guard member comprises a radially inwardly directed collar having an axial aperture therethrough, said collar for engaging the annular recess.

13. A medical device as in claim 12, wherein the aperture through said collar is capable of expansion in cross-sectional area to accommodate the increasing cross-sectional area of the tapered portion of said locking element as said guard is moved axially in a distal direction thereover, until said collar is axially aligned with said annular recess, into which said collar will engage.

14. A safety needle for use with a syringe, comprising:
    a connector adapted to be removably attached to said syringe;
    a needle secured to said connector;
    a tubular guard disposed about said needle and adapted for axial movement from a first position where the tip of said needle is exposed to a second position where the guard covers the tip of the needle to prevent needle sticks; and
    a tubular sheath having one open end;
    wherein said needle and said guard are enclosed within said sheath which is disposed concentrically about said needle and said guard, and is removably secured at its open end in frictional engagement with said connector.

15. A safety needle as in claim 14, further comprising a locking element disposed along the needle for retaining said guard in said second position.

16. A safety needle as in claim 15, wherein said locking element comprises a conical portion extending radially outwardly in the direction of the delivery end of said needle.

17. A medical device, comprising:
    a needle having first and second ends, and adapted to be placed in communication with the delivery end of a syringe by way of said first end;
    a guard axially movable between a first position in which the second end of said needle is exposed, and a second position in which said second end of said needle is shielded; and
    locking means disposed intermediate said first and second ends and distally of the delivery end of said syringe for retaining said guard in said second position.

18. A medical device as in claim 17, further comprising a radially inwardly directed collar on said guard, and an annular recess on said locking means for receiving said collar.

19. A medical device as in claim 17, wherein said locking means is disposed within said guard with said guard in either said first or second position.

* * * * *